(12) United States Patent
Yoshida

(10) Patent No.: US 11,156,350 B2
(45) Date of Patent: Oct. 26, 2021

(54) LIGHT SOURCE DEVICE

(71) Applicant: OLYMPUS CORPORATION, Tokyo (JP)

(72) Inventor: Yusuke Yoshida, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/174,623

(22) Filed: Feb. 12, 2021

(65) Prior Publication Data

US 2021/0164642 A1 Jun. 3, 2021

Related U.S. Application Data

(63) Continuation of application No. PCT/JP2019/005818, filed on Feb. 18, 2019.

(30) Foreign Application Priority Data

Aug. 24, 2018 (JP) .............................. JP2018-157111

(51) Int. Cl.
F21V 29/71 (2015.01)

(52) U.S. Cl.
CPC .................... F21V 29/71 (2015.01)

(58) Field of Classification Search
CPC ......... F21V 29/71; F21V 29/51; F21S 45/49; F21S 45/40
See application file for complete search history.

(56) References Cited

U.S. PATENT DOCUMENTS

| | | | |
|---|---|---|---|
| 2005/0201107 A1* | 9/2005 | Seki | H04N 9/3144 362/373 |
| 2007/0019432 A1* | 1/2007 | Shimada | B60Q 1/124 362/545 |
| 2010/0157606 A1* | 6/2010 | Roucoules | F21S 43/14 362/294 |
| 2016/0291449 A1* | 10/2016 | Masuda | F21V 29/61 |

(Continued)

FOREIGN PATENT DOCUMENTS

| | | |
|---|---|---|
| JP | 2010-102997 A | 5/2010 |
| JP | 2012-008474 A | 1/2012 |
| JP | 2014-045820 A | 3/2014 |

(Continued)

OTHER PUBLICATIONS

International Search Report dated Apr. 10, 2019 issued in PCT/JP2019/005818.

*Primary Examiner* — Zheng Song
(74) *Attorney, Agent, or Firm* — Scully, Scott, Murphy & Presser, P.C.

(57) ABSTRACT

A light source device includes has a configuration in which a height of a heat sink from a reference surface when the reference surface is a bottom surface of a housing is set to be lower than a height of a light source unit from the reference surface, and a heat pipe includes a first heat pipe, a first end part of which is connected with the heat generation body and a second end part of which is connected with the heat sink, and a second heat pipe, a third end part of which is connected with a heat generation body and a fourth end part of which is connected with the heat sink so that a distance to the second end part is longer than a distance between the first end part and the third end part.

5 Claims, 7 Drawing Sheets

(56) References Cited

U.S. PATENT DOCUMENTS

2016/0353984 A1* 12/2016 Shirota .................. A61B 1/128
2018/0310438 A1* 10/2018 Murata .................. F21V 29/57

FOREIGN PATENT DOCUMENTS

| WO | 2014/038352 A1 | 3/2014 |
| WO | WO 2014/034205 A1 | 3/2014 |
| WO | WO 2015/178054 A1 | 11/2015 |

* cited by examiner

LIGHT SOURCE DEVICE

CROSS REFERENCE TO RELATED APPLICATION

This application is a continuation application of PCT/JP2019/005818 filed on Feb. 18, 2019 and claims benefit of Japanese Application No. 2018-157111 filed in Japan on Aug. 24, 2018, the entire contents of which are incorporated herein by this reference.

BACKGROUND OF THE INVENTION

1. Field of the Invention

The present invention relates to a light source device in which a heat generation body in a light source unit is connected with a heat sink through a heat pipe.

2. Description of the Related Art

Typically, an observation object of an endoscope used in, for example, medical and industrial fields is in a dark place such as inside of a body cavity or inside of a device in many cases, and thus a light source device configured to irradiate the object with illumination light is used. Some light source devices of this kind include, as a light source, a solid-state light emitting element such as an LED (light emitting diode) or a laser beam source, and a plurality of solid-state light emitting elements are provided to enable emission of illumination light of a desired color such as white light.

In such a light source device, an amount of heat generated at each solid-state light emitting element tends to be large due to need for emission of a large quantity of illumination light. Thus, in some conventional light source devices, a cooling unit for cooling each solid-state light emitting element as a heat generating source is included inside a housing as disclosed in, for example, Japanese Patent Application Laid-Open Publication No. 2014-45820 and International Publication No. 2014/038352. The cooling unit in such a conventional light source device is typically configured as a structure such as a cooling fan, a heat sink, or a heat pipe.

SUMMARY OF THE INVENTION

A light source device according to an aspect of the present invention includes: a housing; a light source unit disposed at a predetermined height from a bottom surface of the housing; a heat generation body disposed in the light source unit; a heat sink disposed at a predetermined height from the bottom surface of the housing; and a heat pipe connected with the heat generation body and the heat sink. A height of the heat sink from a reference surface when the reference surface is the bottom surface of the housing is set to be lower than a height of the light source unit from the reference surface. The heat pipe includes a first heat pipe, a first end part of which is connected with the heat generation body and a second end part of which is connected with the heat sink, and a second heat pipe, a third end part of which is connected with the heat generation body and a fourth end part of which is connected with the heat sink so that a distance to the second end part is longer than a distance between the first end part and the third end part.

DETAILED DESCRIPTION OF THE PREFERRED EMBODIMENT

Figure 1:
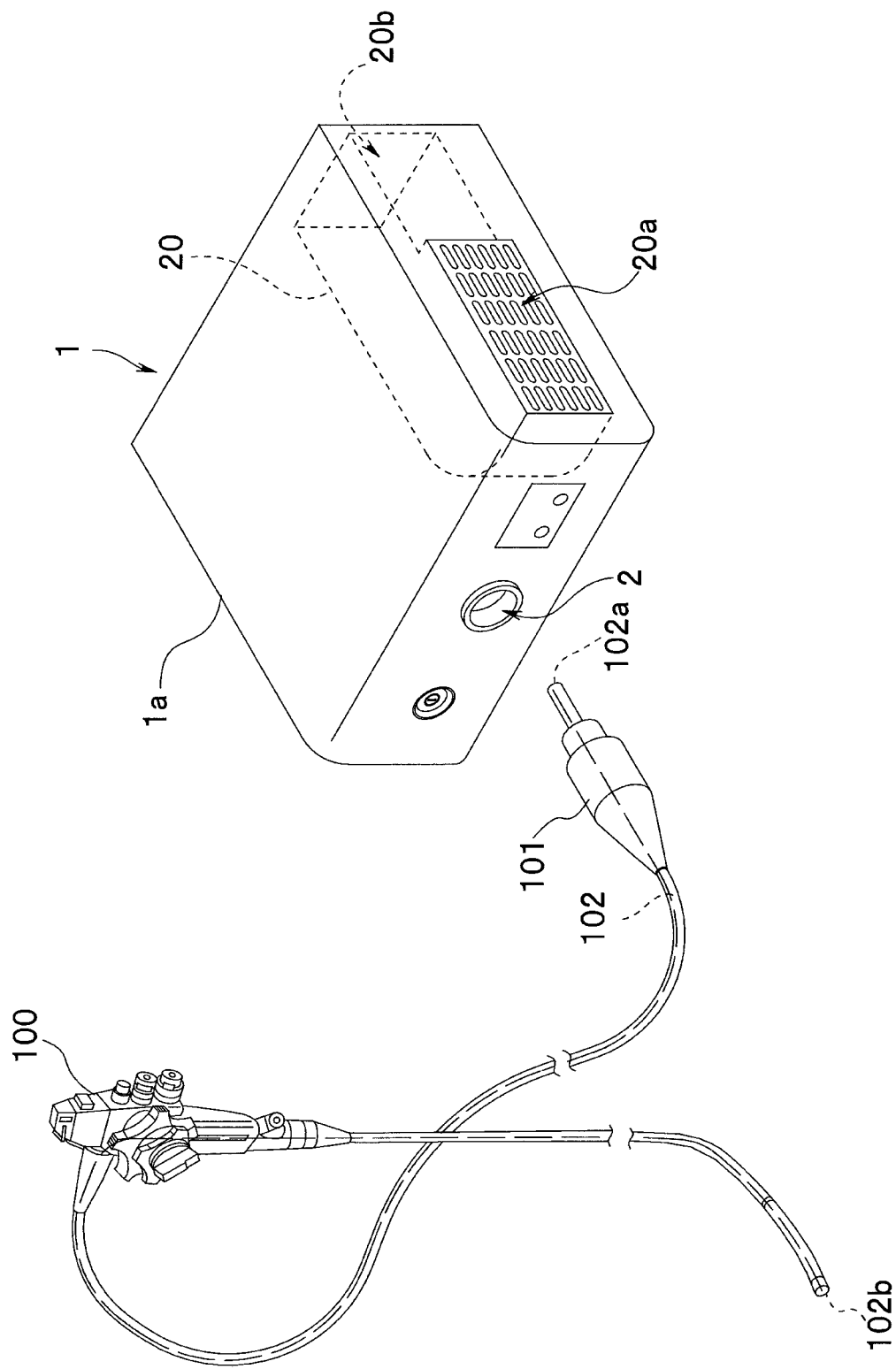
FIG. 1 is an exterior diagram of an endoscope and a light source device.

An embodiment of the present invention will be described below with reference to the accompanying drawings. Each drawing used in description below is schematically illustrated, and dimensional relations, scaling, and the like of members are made different for each component in some cases to illustrate the component in a recognizable size in the drawings. Thus, in the present invention, the number, the shapes, and dimensional ratios of the components, relative positional relations among components, and the like are not limited to those illustrated in the drawings.

A light source device 1 of the present embodiment is a device configured to generate and emit illumination light for illuminating an object observed by using an endoscope 100. The light source device 1 is made of a housing of a substantially rectangular parallelepiped shape and includes various components.

First, a schematic configuration of an endoscope system including the light source device 1 of the present embodiment and an endoscope to which the light source device 1 is applied will be described below mainly with reference to FIG. 1.

The endoscope 100 is a device configured to perform image pickup of an observation site inside a subject such as a living body or a structural object and output and display an image based on acquired image pickup data by using a display device (not illustrated). Note that the configuration of the endoscope 100 is publicly known and similar to the configuration of a conventionally available endoscope, and thus description of the configuration will be omitted.

As illustrated in FIG. 1, the light source device 1 used in connection with the endoscope 100 includes, at a front surface of the housing, a connector part 2 as a connection part with which a plug part 101 provided to the endoscope 100 is connected. One end 102a of an optical fiber cable 102 inserted into the endoscope 100 is disposed at the plug part 101. Light emitted from the light source device 1 to the one end 102a of the optical fiber cable 102 is transmitted through the optical fiber cable 102 and emitted toward a front side from another end 102b of the optical fiber cable 102, which is provided at a distal end portion of the endoscope 100, thereby illuminating an observation object.

The light source device 1 includes a plurality of light sources (not illustrated in FIG. 1) as described later and emits a light beam as a bundle of light emitted from the respective light sources toward the one end 102a of the optical fiber cable 102 of the plug part 101 connected with the connector part 2.

The light source device 1 includes a cooling unit 20 for cooling the plurality of light sources (not illustrated in FIG. 1) as a heat generation body. A housing 1a forming an outline of the light source device 1 is provided with an air inlet 20a as an opening part for introducing, into the housing, air as a cooling medium caused to pass through the cooling unit 20 disposed inside the housing 1a, and an air outlet 20b as an opening part for discharging air inside the housing to outside of the housing.

The air inlet 20a is formed at one side surface of the housing 1a of the light source device 1. The air outlet 20b is formed at a second side surface (in the present embodiment, a back surface) of the housing 1a of the light source device 1, which is adjacent to the one side surface at which the air inlet 20a is formed. Air as a cooling medium flows into the housing 1a of the light source device 1 through the air inlet 20a, passes through the cooling unit 20, and is discharged through the air outlet 20b (to be described later in detail).

Note that, in the present embodiment, the air inlet 20a is provided at the one side surface of the light source device 1 and the air outlet 20b is provided at the back surface as the second side surface adjacent to the one side surface as illustrated in FIG. 1. However, places at which the air inlet 20a and the air outlet 20b are provided are not limited to examples of the present embodiment. Specifically, the air inlet 20a and the air outlet 20b may be each provided at any of front, back, upper, bottom, and side surfaces of the housing 1a of the light source device 1. Alternatively, the air inlet 20a and the air outlet 20b may be provided at the same surface of the housing 1a of the light source device 1.

Note that, in this case, the front surface of the housing 1a of the light source device 1 is a surface at which the connector part 2 is provided. The back surface of the housing 1a is a surface facing the above-described front surface. The side surfaces are two surfaces adjacent to the above-described front surface and the above-described back surface. The bottom surface is a surface disposed on the lower surface side when the housing 1a of the light source device 1 is installed on a predetermined plane in a normal state (state illustrated in FIG. 1), and the upper surface is a surface facing the bottom surface.

Figure 2:
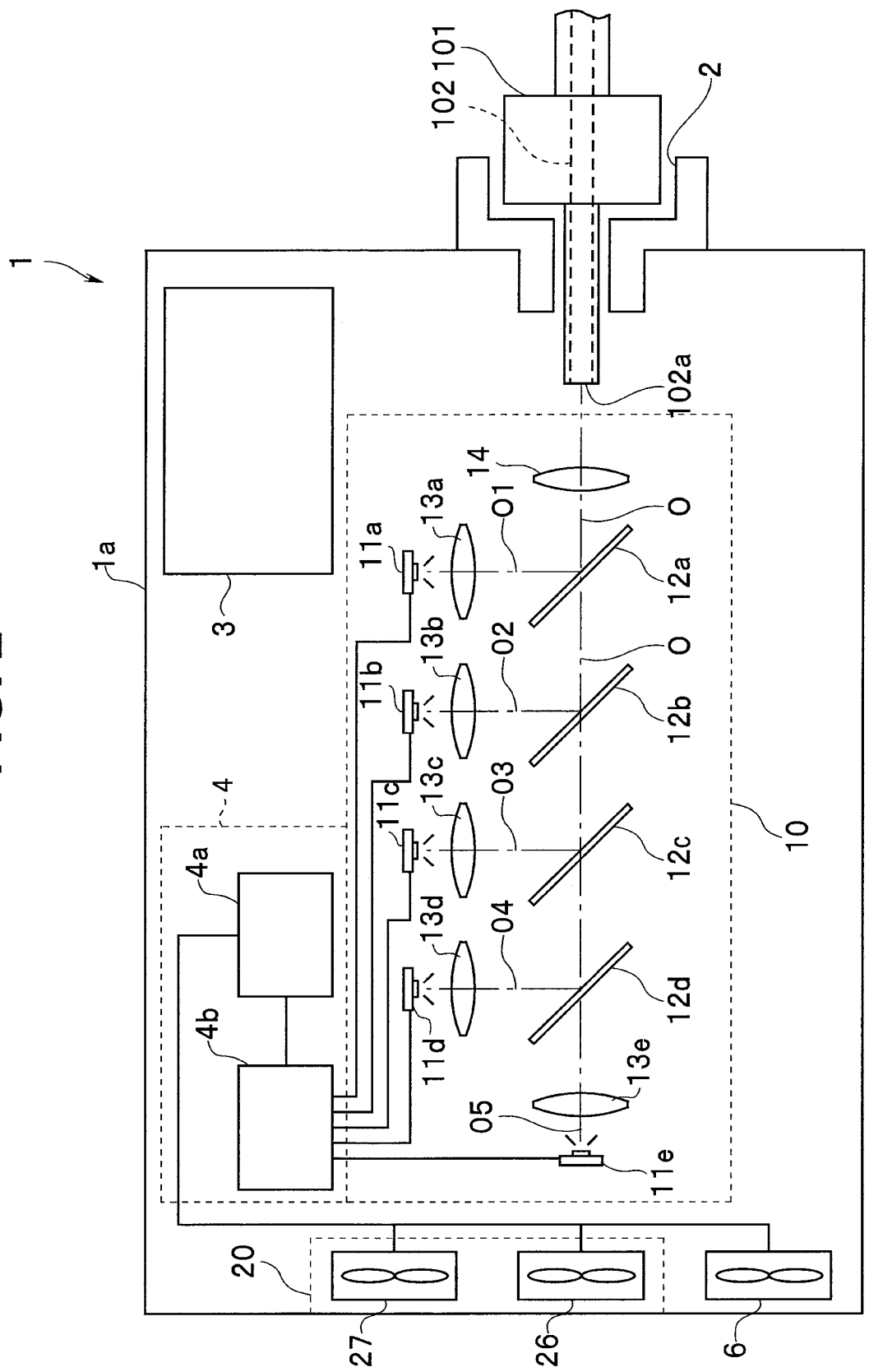
FIG. 2 is a block configuration diagram illustrating a main function of the light source device.

The following describes a main function of the light source device 1 with reference to FIG. 2. Note that FIG. 2 only illustrates a main configuration of electric and optical components of the light source device 1. The components are two-dimensionally disposed so that a relation among the components can be easily understood.

As illustrated in FIG. 2, the light source device 1 of the present embodiment includes a light source unit 10, a power source unit 3, a control unit 4, an in-housing cooling fan 6, and light source cooling fans 26 and 27 as parts of the cooling unit 20. Note that FIG. 2 does not illustrate, for example, a heat releasing unit (heat sink) and a heat transferring unit (heat pipe) among components of the cooling unit 20. A detail configuration of the cooling unit 20 will be described later.

The power source unit 3 is an electrical power supply unit configured to supply electrical power that drives each component unit of the light source device 1. Note that although the power source unit 3 is illustrated at a position separated from the light source unit 10 in FIG. 2, the power source unit 3 is disposed below the light source unit 10 in reality as described later.

The control unit 4 includes a control unit 4a and a light source drive unit 4b. The control unit 4a includes a circuit board on which a control circuit for controlling operation of the light source device 1 based on a predetermined computer program is mounted, and includes a microcomputer including a CPU, a ROM, and a RAM, an auxiliary storage device such as a hard disk drive (HDD) or a solid state drive (SSD), and an input-output interface. The light source drive unit 4b includes a circuit board on which an electric circuit for emitting illumination light by driving a solid-state light emitting element (to be described later) of the light source unit 10 in accordance with an instruction signal from the control unit 4a is mounted.

The light source unit 10 includes a plurality of light emitting units as the plurality of light sources that are a heat generation body. The present embodiment describes an example in which five light emitting units are included. Each light emitting unit has a configuration in which, for example, a solid-state light emitting element, such as a laser diode or a light emitting diode (LED), configured to emit light in a predetermined wavelength band centered at a different wavelength is mounted on a substrate (metal base substrate) in which an insulating layer is provided on a metal (aluminum or copper) and a conductor such as copper is placed on the insulating layer.

Specifically, the light source unit 10 includes, as the light emitting units each including the solid-state light emitting element, for example, a light emitting unit 11a including a red LED, a light emitting unit 11b including an orange LED, a light emitting unit 11c including a green LED, a light emitting unit 11d including a blue LED, and a light emitting unit 11e including a violet LED. Note that the colors (wavelengths) of light emitted by the individual solid-state light emitting elements are not limited to these colors.

The solid-state light emitting element of each light emitting unit is electrically connected with the light source drive unit 4b and drive-controlled by the light source drive unit 4b. Specifically, on-off control of light emission from each solid-state light emitting element is performed by an instruction signal outputted from the light source drive unit 4b. In addition, each solid-state light emitting element changes the intensity of emitted light in accordance with the instruction signal outputted from the light source drive unit 4b.

Light emitted from each of the plurality of light emitting units (11a, 11b, 11c, 11d, and 11e) is turned into parallel light by the corresponding one of a plurality of collimator lenses (13a, 13b, 13c, 13d, and 13e) and then guided to a light condensation lens 14 by dichroic mirrors (12a, 12b, 12c, and 12d). The plurality of collimator lenses (13a, 13b, 13c, 13d, and 13e), the dichroic mirrors (12a, 12b, 12c, and 12d), and the light condensation lens 14 are optical members that guide emission light from the plurality of light emitting units (11a, 11b, 11c, 11d, and 11e) to the connector part 2 as a connection part.

The light condensation lens 14 functions to condense light emitted from the plurality of light emitting units (11a, 11b, 11c, 11d, and 11e) onto the one end 102a of the optical fiber cable 102 of the plug part 101 connected with the connector part 2. That is, in the light source unit 10 of the light source device 1 in the present embodiment, when an optical axis O is an axis passing through the center of the light condensation lens 14, one light emitting unit 11e is disposed on the optical axis O, and the other four light emitting units (11a, 11b, 11c, and 11d) are disposed at adjacent positions off the optical axis O. The optical axis O is a central axis of light emitted from the light source unit 10.

When central axes of light emitted from the plurality of respective light emitting units (11a, 11b, 11c, 11d, and 11e) are denoted by reference signs O1, O2, O3, O4, and O5, the axis denoted by the reference sign O5 is parallel to the optical axis O. The four light emitting units (11a, 11b, 11c, and 11d) are disposed so that the corresponding other four central axes (reference signs O1, O2, O3, and O4) are orthogonal to the optical axis O.

Specifically, the four light emitting units (11a, 11b, 11c, and 11d) other than the light emitting unit 11e are disposed on the same plane including the optical axis O so that the axes denoted by the reference signs O1, O2, O3, and O4 are orthogonal to the optical axis O. The other four light emitting units (11a, 11b, 11c, and 11d) are also disposed side by side in a direction parallel to the optical axis O on the same side (upper position in FIG. 2) of the optical axis O on the same plane including the optical axis O.

The plurality of collimator lenses (13a, 13b, 13c, 13d, and 13e) are each disposed on the front side of the corresponding one of the plurality of light emitting units (11a, 11b, 11c, 11d, and 11e), in other words, on an optical path through which emission light passes. Accordingly, emission light from each of the light emitting units (11a, 11b, 11c, 11d, and 11e) is transmitted through the collimator lenses (13a, 13b, 13c, 13d, and 13e) and emitted as parallel light.

The plurality of dichroic mirrors (12a, 12b, 12c, and 12d) are each provided on the front side of the corresponding one of the four collimator lenses (13a, 13b, 13c, and 13d) among the plurality of collimator lenses (13a, 13b, 13c, 13d, and 13e), in other words, on the optical path of emission light.

The dichroic mirrors (12a, 12b, 12c, and 12d) are disposed at a predetermined interval along the optical axis O. Reflection surfaces of the respective dichroic mirrors (12a, 12b, 12c, and 12d) are orthogonal to a plane including the optical axis O and the central axes O1, O2, O3, and O4 and are tilted substantially at 45° relative to the optical axis O on the plane.

In this case, the reflection surfaces of the dichroic mirrors (12a, 12b, 12c, and 12d) are disposed toward the respective other four light emitting units (11a, 11b, 11c, and 11d) and the light condensation lens 14. Accordingly, the reflection surfaces of the dichroic mirrors (12a, 12b, 12c, and 12d) each reflect, toward the light condensation lens 14, emission light from the corresponding one of the other four light emitting units (11a, 11b, 11c, and 11d).

The reflection surface of the dichroic mirror 12a among the plurality of dichroic mirrors reflects light in a predetermined wavelength band including the wavelength of emission light from the light emitting unit 11a and transmits light in the other wavelength band. The reflection surface of the dichroic mirror 12b reflects light in a predetermined wavelength band including the wavelength of emission light from the light emitting unit 11b and transmits light in the other wavelength band. The reflection surface of the dichroic mirror 12c reflects light in a predetermined wavelength band including the wavelength of emission light from the light emitting unit 11c and transmits light in the other wavelength band. The reflection surface of the dichroic mirror 12d reflects light in a predetermined wavelength band including the wavelength of emission light from the light emitting unit 11d and transmits light in the other wavelength band. The dichroic mirrors (12a, 12b, 12c, and 12d) transmit light in a predetermined wavelength band including a wavelength of emission light from the light emitting unit 11e.

Parallel light emitted from the plurality of light emitting units (11a, 11b, 11c, and 11d) and emitted through the plurality of collimator lenses (13a, 13b, 13c, and 13d) is reflected by the dichroic mirrors 12a, 12b, 12c, and 12d and synthesized with parallel light emitted from the light emitting unit 11e and emitted through the collimator lens 13e, and then is incident on the light condensation lens 14.

In the light source unit 10 having a configuration as described above, the plurality (five) of light emitting units (11a, 11b, 11c, 11d, and 11e) are disposed so that the central axes of light emitted from the respective light emitting units are positioned on the same plane. In addition, the light emitting units (11a, 11b, 11c, 11d, and 11e) are sequentially arrayed in a predetermined direction along the optical axis O. Note that the number of light emitting units included in the light source unit 10 is not limited to the above-described example (five) but may be, for example, equal to or larger than two.

Figure 3:
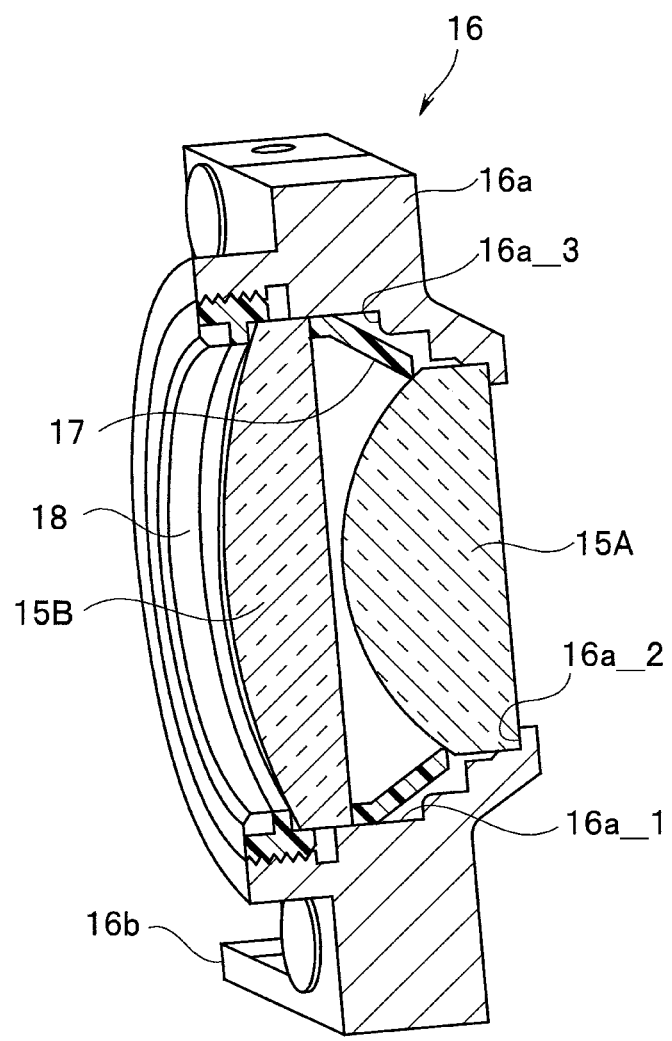
FIG. 3 is a perspective view illustrating the configuration of a lens frame.

In the present embodiment, the collimator lens (13a, 13b, 13c, 13d, and 13e) and the light condensation lens 14 each have a configuration in which two lenses are assembled to a lens frame. Each lens frame basically has the same configuration and is, for example, a lens frame 16 in the configuration illustrated in FIG. 3. The lens frame 16 in FIG. 3 includes a frame body 16a holding a lens 15A and a lens 15B having a diameter larger than the diameter of the lens 15A, and a fixation base 16b integrally provided at a base part of the frame body 16a.

The two lenses 15A and 15B are housed in the frame body 16a through a lens fixation collar 17 and fixed to the frame body 16a by a fixation ring 18. Specifically, an opening hole for housing the lenses 15A and 15B is provided at the frame body 16a, one side of the opening hole forms a lens insertion opening 16a_1 into which the lenses 15A and 15B are inserted, and the other side of the opening hole forms a holding part 16a_2 that contacts and holds an outer peripheral part of the lens 15A having a smaller diameter.

Specifically, the lens 15A is inserted through the lens insertion opening 16a_1, the outer peripheral part of the lens 15A is made contact with the holding part 16a_2, and then the lens fixation collar 17 and the lens 15B are sequentially inserted. Then, in a state in which the lens 15A and the lens 15B are held at a defined interval by the lens fixation collar 17, a male screw provided at an outer periphery of the fixation ring 18 is screwed into a female screw provided on an inner peripheral side of the lens insertion opening 16a_1, thereby fixing the lenses 15A and 15B in the frame body 16a with predetermined pressing force.

In this case, the lens fixation collar 17 is interposed at an outer peripheral part between the lenses 15A and 15B having outer diameters different from each other, and thus formed as a cylinder of a substantially circular truncated cone shape. With this configuration, when the lens fixation collar 17 is wrongly inserted in an opposite orientation through the lens insertion opening 16a_1 to fix the lenses 15A and 15B to the frame body 16a, the lens fixation collar 17 is disposed in an opposite orientation between the lenses 15A and 15B and the interval between the lenses 15A and 15B is inappropriate, and accordingly, appropriate optical performance cannot be obtained.

To prevent such wrong assembly due to insertion of the lens fixation collar 17 in the opposite orientation, a shoulder part 16a_3 that can contact an end face of the lens fixation collar 17 on a large-diameter side is provided at a predetermined position on the lens insertion opening 16a_1 of the frame body 16a in the present embodiment.

When the lens fixation collar 17 is inserted in a correct orientation through the lens insertion opening 16a_1, the lens fixation collar 17 does not contact the shoulder part 16a_3, but an end face of the lens fixation collar 17 on a small-diameter side contacts the outer peripheral part of the lens 15A, and the end face of the lens fixation collar 17 on the large-diameter side contacts the outer peripheral part of the lens 15A. Accordingly, the lenses 15A and 15B can be held at the defined interval through the lens fixation collar 17.

When the lens fixation collar 17 is inserted through the lens insertion opening 16a_1 in an orientation opposite to the normal orientation, the lens fixation collar 17 does not contact the lens 15A but the end face of the lens fixation collar 17 on the large-diameter side contacts the shoulder part 16a_3. When the lens 15B is inserted in this state, the end face of the lens fixation collar 17 on the small-diameter side contacts a back surface side of the lens 15B, and the lens 15B protrudes from the frame body 16a so that the fixation ring 18 cannot be screwed into the frame body 16a. Thus, an operator can easily notice that the lens fixation collar 17 is assembled in the opposite orientation, and can avoid a defect.

The following describes the in-housing cooling fan 6 and the light source cooling fans 26 and 27. The in-housing cooling fan 6 is an electric fan for discharging air inside the housing 1a of the light source device 1 to outside. The in-housing cooling fan 6 is drive-controlled by the control unit 4a. Specifically, the control unit 4a performs control to, for example, change a rotation speed of the in-housing cooling fan 6 by controlling drive of the in-housing cooling fan 6. Note that the number of in-housing cooling fans 6 is not limited to one but a plurality of in-housing cooling fans 6 may be provided.

The light source cooling fans 26 and 27 are electric fans included in the cooling unit 20 to be described later. The light source cooling fans 26 and 27 are drive-controlled by the control unit 4a. That is, the control unit 4a performs control to, for example, change rotation speeds of the light source cooling fans 26 and 27 by controlling drive of the light source cooling fans 26 and 27. Note that three or more light source cooling fans may be provided.

The control unit 4a detects intake air temperature in the housing 1a and changes the rotation speeds of the light source cooling fans 26 and 27 at stages in accordance with the intake air temperature. The control unit 4a performs control so that the rotation speeds of the light source cooling fans 26 and 27 are low when the intake air temperature in the housing 1a is relatively low but the rotation speeds of the light source cooling fans 26 and 27 increase as the intake air temperature increases.

The light source cooling fans 26 and 27 are downsized and disposed close to each other. Thus, when the light source cooling fans 26 and 27 are controlled to the same rotation speed, there is actually a slight difference between the rotation speeds of the fans, and accordingly, two sound waves close to each other interfere and howling potentially occurs. Thus, the control unit 4a intentionally drives the light source cooling fans 26 and 27 at rotation speeds shifted from each other, thereby reducing noise due to the howling.

Figure 4:
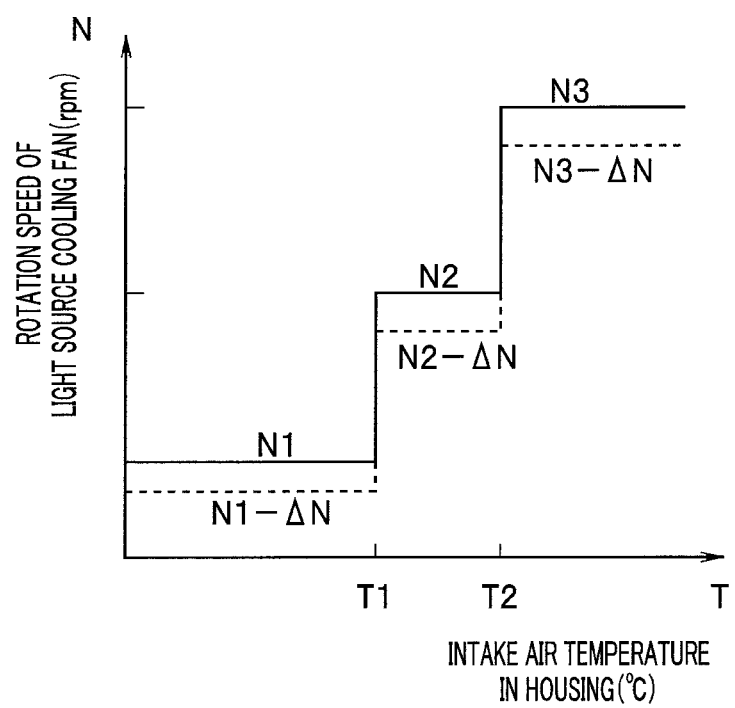
FIG. 4 is an explanatory diagram illustrating a drive characteristic of a light source cooling fan.

For example, as illustrated in FIG. 4, when controlling a rotation speed N of one of the light source cooling fans 26 and 27 to N1 for an intake air temperature T in the housing 1a<T1, N2 for T1≤T≤T2, or N3 for T>T2 (for example, T1=30° C., T2=35° C., N1=2900 rpm, N2=3900 rpm, and N3=5500 rpm), the control unit 4a controls the rotation speed of the other of the light source cooling fans 26 and 27 to a rotation speed lower by ΔN (for example, ΔN=300 rpm). Accordingly, howling due to interference between sounds from the light source cooling fans 26 and 27 disposed close to each other can be reduced, and noise can be reduced.

Figure 5:
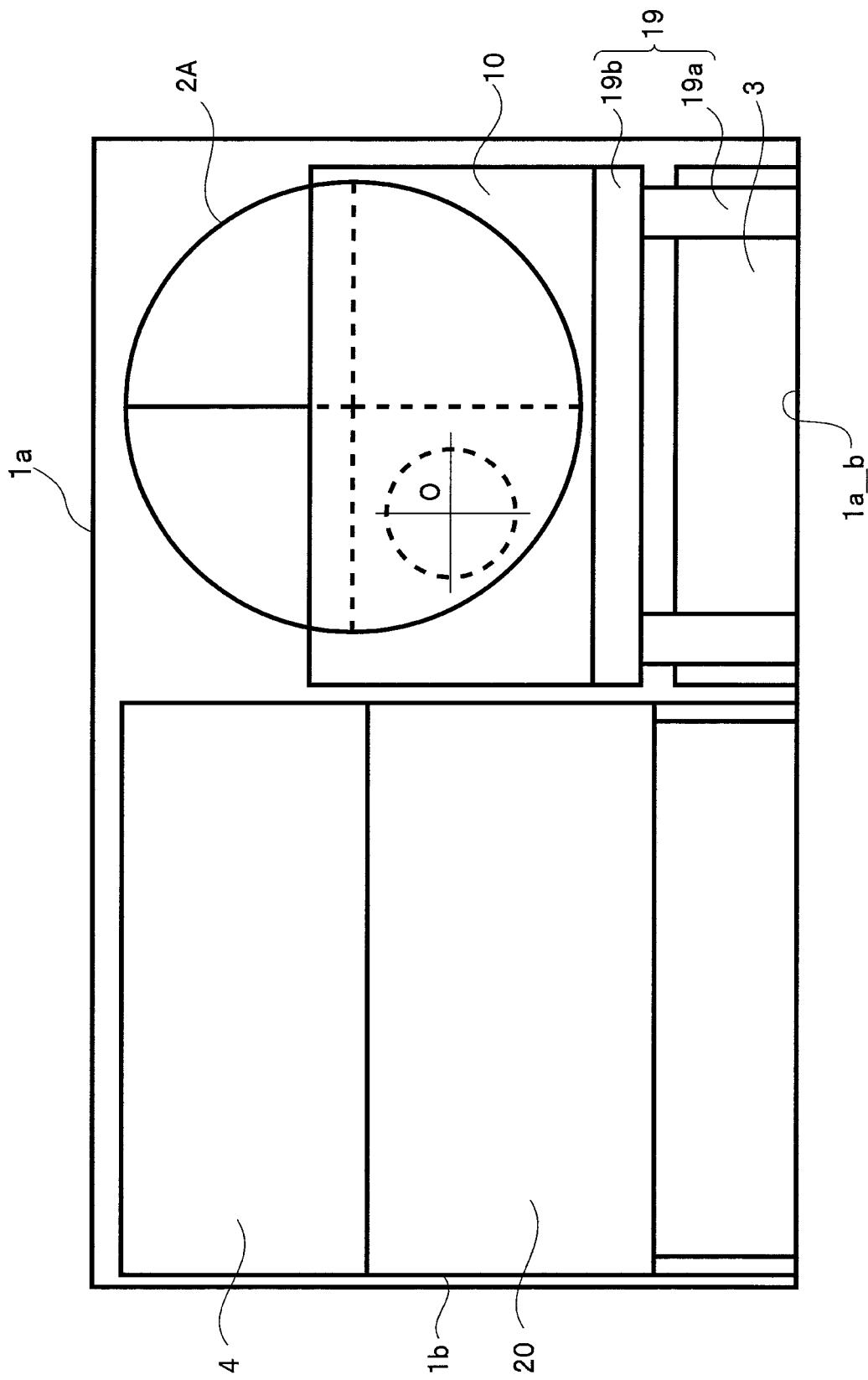
FIG. 5 is an explanatory diagram illustrating disposition of each unit in the light source device in an up-down direction.

Specifically, the above-described units (the power source unit 3, the control unit 4, the light source unit 10, and the cooling unit 20) in the main configuration of the light source device 1 are disposed as illustrated in FIG. 5 in the housing 1a of the light source device 1. FIG. 5 illustrates disposition of the units when viewed from the back surface side of the housing 1a. The units (the power source unit 3, the control unit 4, the light source unit 10, and the cooling unit 20) are disposed to allow effective utilization of a space in the housing 1a, in particular, a space in a height direction.

The power source unit 3 is disposed on a bottom surface 1a_b on the connector part 2 side in the housing 1a, and the light source unit 10 is disposed in a space above the power source unit 3 so that the optical axis O coincides with a central axis of the connector part 2. The light source unit 10 is covered by a dust-proof cover (not illustrated) and fixed above the power source unit 3 through a support frame 19.

The support frame 19 includes a support leg 19a that is fixed to the bottom surface 1a_b of the housing 1a and is slightly longer than a height of the power source unit 3, and a support table 19b to which the light source unit 10 is fixed. A space in the housing 1a in the height direction can be effectively utilized by using the support frame 19 to hold the light source unit 10 at a predetermined height from the bottom surface 1a_b of the housing 1a so that the power source unit 3 is disposed below the light source unit 10.

Note that an observation switching unit 2A for performing switching between observation modes such as a white light mode and a fluorescence mode is disposed on an incident side of the connector part 2 on which emission light from the light source unit 10 is incident. The observation switching unit 2A includes a plurality of optical filters corresponding to the observation modes and switches, by rotation, optical filters inserted on an optical path of light incident on the connector part 2.

The cooling unit 20 and the control unit 4 are disposed beside the power source unit 3 and the light source unit 10 in the housing 1a. The cooling unit 20 has a configuration in which the heat releasing unit (heat sink) and the heat transferring unit (heat pipe) to be described later are housed in a chamber 1b disposed inside the housing 1a.

The chamber 1b is positioned at a predetermined height separated from the bottom surface 1a_b of the housing 1a and is set so that a height from the bottom surface 1a_b of the housing 1a to an upper end of the chamber 1b is equal to or smaller than a height from the bottom surface 1a_b of the housing 1a to an upper end of the light source unit 10. That is, the chamber 1b is set to provide, between a bottom surface of the chamber 1b and the bottom surface of the housing 1a, a flow path through which air as a cooling medium flowing in through the air inlet 20a is guided to the power source unit 3 and to provide a space in which the control unit 4 is housed above the chamber 1b, and thus the light source device 1 can be downsized in the height direction.

Figure 6:
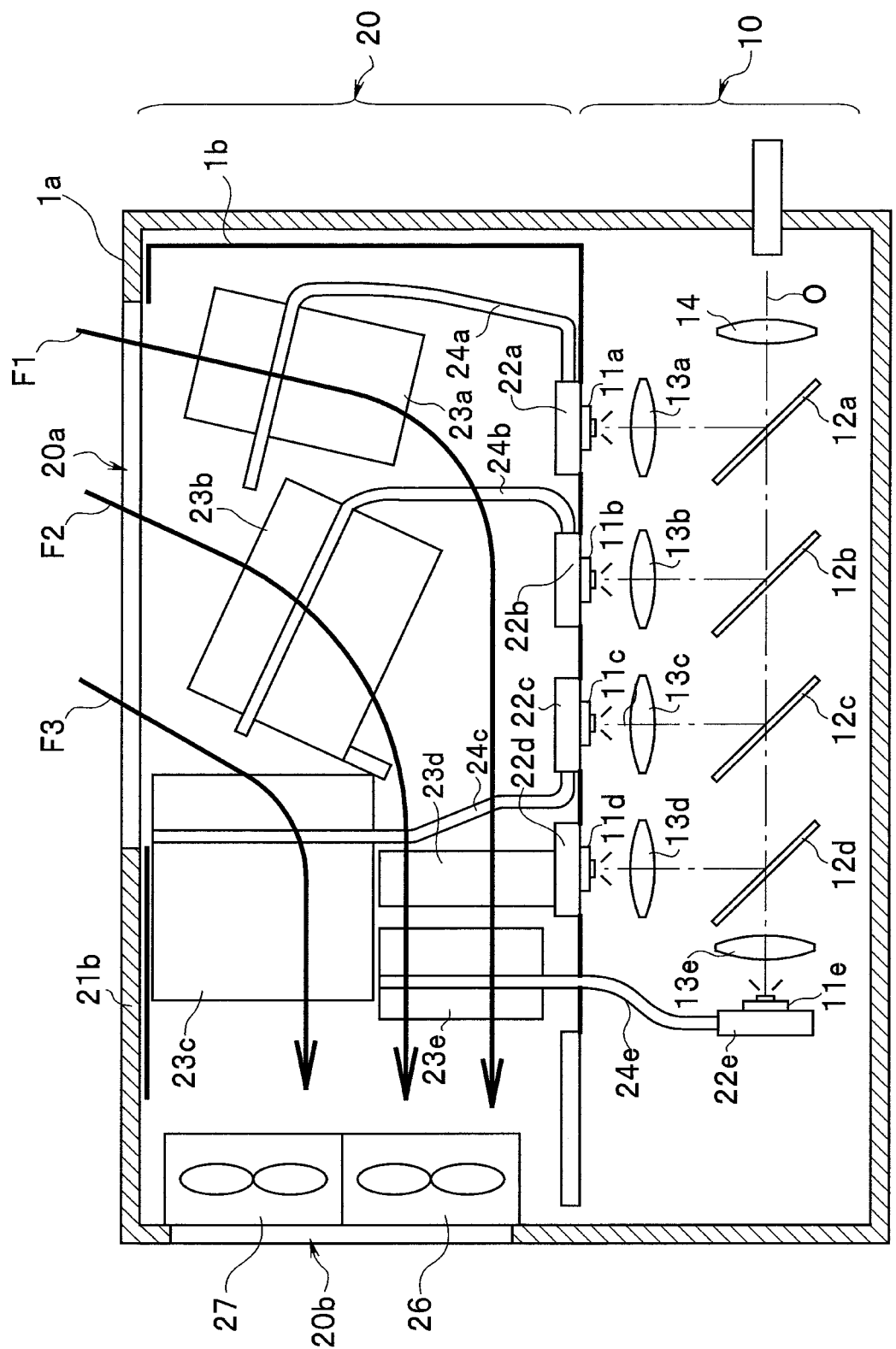
FIG. 6 is an explanatory diagram illustrating disposition of a cooling unit in the light source device.

The following describes the cooling unit 20. As illustrated in FIG. 6, the cooling unit 20 is a component unit for cooling, among the components of the light source unit 10, the light emitting units (11a, 11b, 11c, 11d, and 11e) including solid-state light emitting elements as light sources that are a heat generation body. The cooling unit 20 includes a plurality of heat receiving parts (22a, 22b, 22c, 22d, and 22e), a plurality of heat sinks (23a, 23b, 23c, 23d, and 23e) as a plurality of heat releasing units, and a plurality of heat pipes (24a, 24b, 24c, and 24e) as a plurality of heat transferring units, etc.

The plurality of heat receiving parts (22a, 22b, 22c, 22d, and 22e) are fixed in contact on the back surface side of the plurality of respective light emitting units (11a, 11b, 11c, 11d, and 11e). The plurality of heat receiving parts (22a, 22b, 22c, 22d, and 22e) are heat conduction members provided to transfer heat from the solid-state light emitting elements of the plurality of light emitting units (11a, 11b, 11c, 11d, and 11e).

The plurality of heat receiving parts are the heat receiving part 22a provided on the back surface side of the light emitting unit 11a to conduct heat generated at the light emitting unit 11a, the heat receiving part 22b provided on the back surface side of the light emitting unit 11b to conduct heat generated at the light emitting unit 11b, the heat receiving part 22c provided on the back surface side of the light emitting unit 11c to conduct heat generated at the light emitting unit 11c, the heat receiving part 22d provided on the back surface side of the light emitting unit 11d to conduct heat generated at the light emitting unit 11d, and the heat receiving part 22e provided on the back surface side of the light emitting unit 11e to conduct heat generated at the light emitting unit 11e.

Note that the plurality of heat receiving parts and the plurality of light emitting units may be disposed in contact, but as another form, for example, a member having a high heat-transfer coefficient may be interposed between each heat receiving part and the corresponding light emitting unit. Although the present embodiment describes an example in which the plurality of heat receiving parts are each disposed on the back surface side of the corresponding one of the plurality of light emitting units, the present invention is not limited to this configuration. The disposition and shape of each heat receiving part corresponding to a light emitting unit may be such that the heat receiving part does not intersect a light emission surface of the light emitting unit, and the heat receiving part is allowed to have any shape.

The chamber 1b houses the plurality of heat sinks (23a, 23b, 23c, 23d, and 23e) as a plurality of heat releasing units and the plurality of heat pipes (24a, 24b, 24c, and 24e) as a plurality of heat transferring units. The chamber 1b includes opening parts on the air inlet 20a side and the air outlet 20b side of the housing 1a and forms a duct through which gas (air in a normal case; hereinafter simply referred to as air) as a cooling medium for cooling the plurality of light emitting units (11a, 11b, 11c, 11d, and 11e) of the light source unit 10 passes.

The cooling medium (air) flows in through the air inlet 20a of the housing 1a, flows in the direction in which the plurality of light emitting units (11a, 11b, 11c, 11d, and 11e) are arrayed in the chamber 1b, and is discharged through the air outlet 20b provided at the second side surface of the housing 1a. In FIG. 6, directions in which air flows in the chamber 1b are illustrated with arrows F1, F2, and F3.

The plurality of heat sinks as a plurality of heat releasing units are disposed at respective predetermined positions in an air flow path formed in the chamber 1b. The cooling unit 20 in the present embodiment includes the heat sinks (23a, 23b, 23c, 23d, and 23e) with the a number equal to the number of the plurality of heat receiving parts (that is, plurality of light emitting units), which is five.

A surface of the heat sink through which air passes in each of the three heat sinks (23a, 23b, and 23c) disposed near the air inlet 20a among the plurality of heat sinks is disposed at a predetermined tilt angle relative to an inlet surface of the air inlet 20a (one side surface of the housing 1a) in the housing. Each tilt angle is an angle larger than 0° and equal to or smaller than 90° relative to the inlet surface (one side surface of the housing 1a).

In this case, for example, the tilt angle of the air passing surface relative to the inlet surface is set to be more gradual (smaller) for a heat sink disposed on a side far from the air outlet 20b than for a heat sink disposed on a side close to the air outlet 20b. Similarly, the tilt angle of the air passing surface of a heat sink disposed on the side close to the air outlet 20b relative to the inlet surface is set to be most steep (largest). In this manner, the tilt angle of the air passing surface of each of the heat sinks (23a, 23b, and 23c) relative to the inlet surface can be adjusted to achieve smooth flow of the cooling medium (air) flowing through the corresponding one of the flow paths (F1, F2, and F3).

The other heat sinks (23d and 23e) among the plurality of heat sinks are disposed on a flow path of air passing through the heat sinks (23a and 23b) and cooled by air passing through the heat sinks (23a and 23b).

In the light source device 1 of the present embodiment, the plurality of heat sinks are formed to have sizes different from one another as illustrated in FIG. 6 as well. The size of each heat sink is indicated by area of a cross section through which air as the cooling medium passes and surface area of the cross section. The size of the heat sink defines cooling performance.

A heat generation amount and a maximum temperature up to which operation is guaranteed are different among the plurality of solid-state light emitting elements as a heat generation body in the light source device 1, depending on the wavelength of emitted light. Thus, it is possible to obtain a more efficient cooling effect and prevent increase in the size of the device by setting cooling performance of the heat sinks in accordance with a ratio of the heat generation amount relative to the maximum temperature up to which operation is guaranteed for the solid-state light emitting elements.

The cooling performance of each heat releasing unit (heat sink) in the cooling unit 20 can be defined by the magnitudes of the area of a cross section through which air as the cooling medium passes and the surface area of the cross section. Thus, it is possible to achieve higher cooling capacity by increasing the area of the cross-section of the heat releasing unit (heat sink) through which air passes and the surface area of the cross section.

Thus, in the light source device 1 of the present embodiment, the sizes of the five heat sinks are defined in accordance with cooling degrees necessary for the solid-state light emitting elements applied to the plurality of light emitting units (11a, 11b, 11c, 11d, and 11e).

Specifically, in the present embodiment, for example, the three heat sinks (23a, 23b, and 23c) disposed on an upstream side in the air flow path (in the vicinity of the air inlet 20a) among the plurality of heat sinks are connected, through the heat pipes (24a, 24b, and 24c), with the heat receiving parts (22a, 22b, and 22c) of the light emitting units (11a, 11b, and 11c) including respective solid-state light emitting elements having relatively large ratios of the heat generation amount relative to the maximum temperature up to which operation is guaranteed.

Light emitting units including respective solid-state light emitting elements having relatively small ratios of the heat generation amount relative to the maximum temperature up to which operation is guaranteed, namely the light emitting units (11d and 11e) are connected with the heat sinks (23d and 23e) disposed on a downstream side in the flow path. However, the heat sink 23d can be made directly contact with the heat receiving part 22d of the light emitting unit 11d, and thus does not need a heat pipe. The heat sink 23e position separated from the light emitting unit 11e is connected with the light emitting unit 11e of the heat receiving part 22e through the heat pipe 24e.

These plurality of heat pipes (24a, 24b, 24c, and 24e) are disposed substantially orthogonal to a flowing direction in the flow path of the cooling medium (air), in other words, across flow of the air in the flow path. In addition, in an optical system in which the optical axis O of the light source unit 10 and the central axes (O1, O2, O3, O4, and O5) of emission light from the plurality of light emitting units (11a, 11b, 11c, 11d, and 11e) are disposed on the same plane, the plurality of heat pipes (24a, 24b, 24c, and 24e) are routed in the plane to avoid mutual overlapping in a direction of gravity. Accordingly, a height of the housing 1a can be reduced to downsize the light source device 1.

As described above, the height of the chamber 1b of the cooling unit 20 from the bottom surface 1a_b of the housing 1a is set to be lower than the light source unit 10, and heights of the heat sinks (23a, 23b, 23c, 23d, and 23e) from the bottom surface 1a_b of the housing 1a are lower than the light source unit 10. Thus, central positions of the heat sinks (23a, 23b, 23c, and 23e) connected with the heat receiving parts (22a, 22b, 22c, and 22e) through the heat pipes (24a, 24b, 24c, and 24e) in the height direction are lower than the heat receiving parts (22a, 22b, 22c, and 22e).

Thus, the heat pipes (24a, 24b, 24c, and 24e) are configured as sets of a plurality of heat pipes with taken into account a positional relation between a heat generating source (the solid-state light emitting elements) and each heat releasing unit (heat sink), and are each connected with the corresponding heat sink. In the present embodiment, the heat pipes (24a, 24b, 24c, and 24e) are configured as sets of two heat pipes of a first heat pipe and a second heat pipe.

Figure 7:
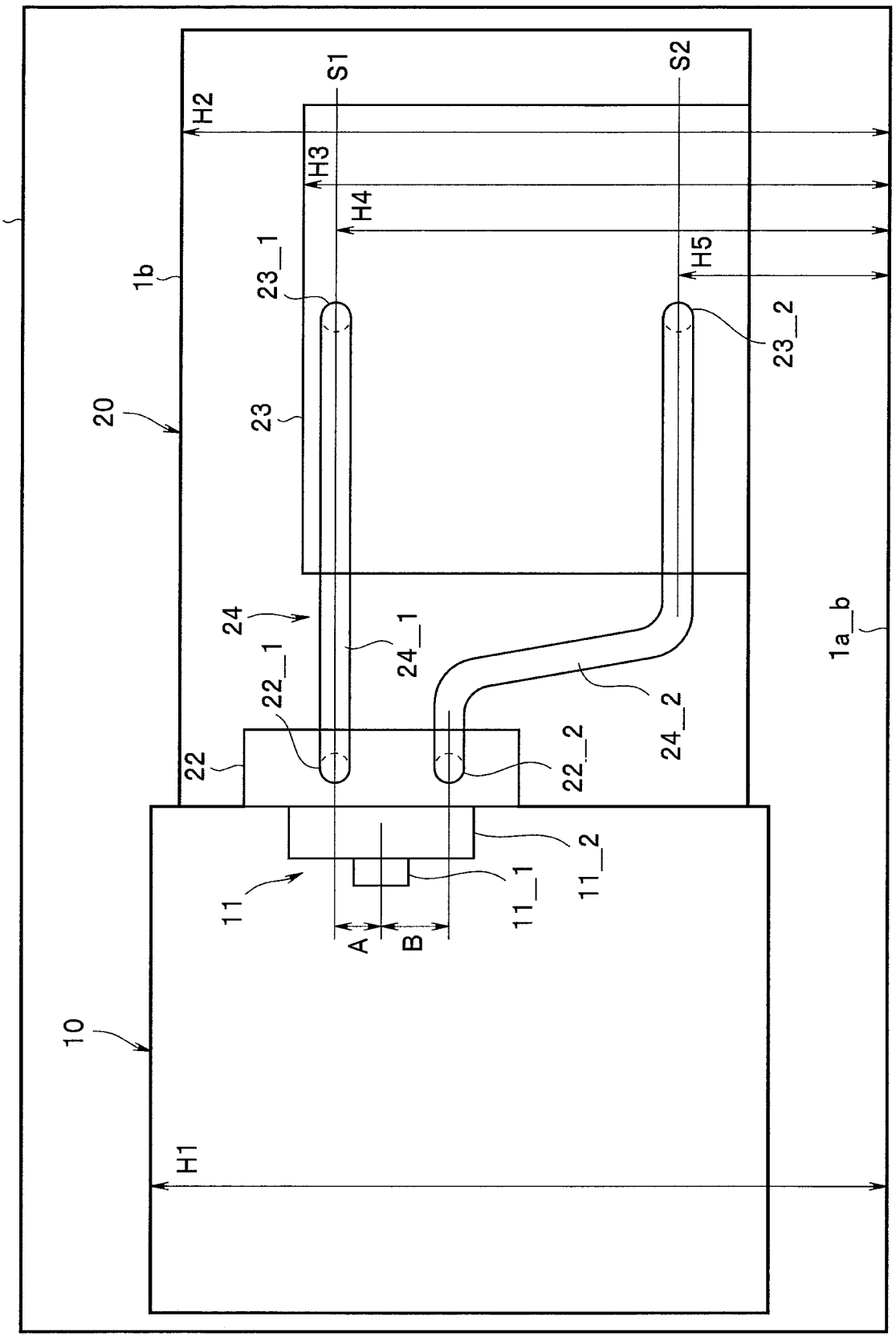
FIG. 7 is an explanatory diagram illustrating a relation among heights of components.

In the following, the plurality of heat pipes (24a, 24b, 24c, and 24e) as sets of two heat pipes, the plurality of light emitting units (11a, 11b, 11c, and 11e), the heat receiving parts (22a, 22b, 22c, and 22e), and the plurality of heat sinks (23a, 23b, 23c, and 23e) are represented by a heat pipe 24, a light emitting unit 11, a heat receiving part 22, and a heat sink 23 as illustrated in FIG. 7, and a connection relation among the heat pipe 24, the light emitting unit 11, the heat receiving part 22, and the heat sink 23 will be described below.

As illustrated in FIG. 7, the heat receiving part 22 is fixed on the back surface side of a substrate 11-2 on which a solid-state light emitting element 11_1 of the light emitting unit 11 is mounted, and the heat receiving part 22 is connected with one end of the heat pipe 24 made of a first heat pipe 24_1 and a second heat pipe 24_2. The other end of each of the first heat pipe 24_1 and the second heat pipe 24_2 is connected with the same heat sink 23.

Specifically, the first heat pipe 24_1 has one end connected with a first connection part 22_1 of the heat receiving part 22 and extended substantially in a horizontal direction, and is disposed in a shape in accordance with disposition of the corresponding heat sink 23 in a first surface S1 parallel to a plane extended substantially in the horizontal direction, in other words, the bottom surface 1a_b of the housing 1a. The other end of the first heat pipe 24_1 is connected with and fixed to a first fixation part 23_1 of the corresponding heat sink 23. The first fixation part 23_1 of the heat sink 23 and the first connection part 22_1 of the heat receiving part 22 are positioned on the same first surface S1.

Note that the first heat pipe 24_1 is desirably horizontally disposed on the first surface S1 at each of the plurality of heat pipes (24a, 24b, 24c, and 24e), but for example, at least one first heat pipe such as a first heat pipe corresponding to a light emitting unit having a relatively large heat generation amount may be horizontally disposed on the first surface S1.

The second heat pipe 24_2 has one end connected with a second connection part 22_2 of the heat receiving part 22 and is extended while curving downward in the direction of gravity. The second connection part 22_2 is provided at a position lower than the first connection part 22_1 in the direction of gravity. The second heat pipe 24_2 is extended from the second connection part 22_2 while curving downward in the direction of gravity and is then connected with and fixed to a second fixation part 23_2 provided at a position lower than the first fixation part 23_1 of the heat sink 23 in the direction of gravity, in other words, on a second surface S2 substantially parallel to the first surface S1 on which the first heat pipe 24_1 is disposed.

Note that, in the present embodiment, the second heat pipe 24_2 is disposed in a vertical plane substantially the same as a vertical plane of the first heat pipe 24_1, but may not be disposed in a vertical plane the same as the vertical plane of the first heat pipe 24_1 as long as the second heat pipe 24_2 does not overlap with the other second heat pipe in the direction of gravity.

A substrate 11_2 on which the solid-state light emitting element 11_1 of the light emitting unit 11 is mounted is held substantially orthogonal to the bottom surface 1a_b of the housing 1a. In the heat receiving part 22 on the back surface side of the substrate 11_2, the first connection part 22_1 of the first heat pipe 24_1 and the second connection part 22_2 of the second heat pipe 24_2 are vertically disposed across a solid-state light emitting element 11_. In addition, a distance A between the first connection part 22_1 and the solid-state light emitting element 11_1 in a vertical direction and a distance B between the second connection part 22_2 and the solid-state light emitting element 11_1 in the vertical direction are set to satisfy a relation of A<B.

Thus, the first heat pipe 24_1 connected with the heat receiving part 22 at a position closer to the solid-state light emitting element 11_1 as a heat generation body is configured as a heat pipe having heat transfer performance higher than heat transfer performance of the second heat pipe 24_2 connected with the heat receiving part 22 at a position relatively separated from the solid-state light emitting element 11_1. For example, the first heat pipe 24_1 is a heat pipe including a wick of a composite structure, thereby enabling efficient heat transfer in the horizontal direction. The second heat pipe 24_2 is a heat pipe including a wick formed of a sintered metal, thereby ensuring heat transfer performance in the direction of gravity.

A relation among the first heat pipe 24_1 and the second heat pipe 24_2 and the first fixation part 23_1 and the second fixation part 23_2 of the heat sink 23 is a relation as described below based on a relation between the housing 1a forming the outline of the light source device 1 and the chamber 1b forming a ventilation duct of the cooling unit 20.

In FIG. 7, when H1 represents a height from a reference surface to an upper end part of the light source unit 10 when the reference surface is the bottom surface 1a_b of the housing 1a, H2 represents a height from the reference surface to an upper end part of the chamber 1b, H3 represents a height from the reference surface to an upper end part of the heat sink 23, H4 represents a height from the reference surface to the first fixation part 23_1 of the first heat pipe 24_1 (height from the reference surface to the first surface S1), and H5 represents a height from the reference surface to the second fixation part 23_2 of the second heat pipe 24_2 (height from the reference surface to the second surface S2), the heights (H1, H2, H3, H4, H5) are set to have a relation indicated by Inequality (1) below.

$$H1 \geq H2 > H3 > H4 > H5 \tag{1}$$

The height H4 from the reference surface to the first fixation part 23_1 of the first heat pipe 24_1 is substantially equal to a height from the reference surface to the first connection part 22_1 of the heat receiving part 22. In addition, as described above, the distance A between the first connection part 22_1 and the solid-state light emitting element 11_1 in the vertical direction is set to have a relation indicated by Inequality (2) below with the distance B between the second connection part 22_2 and the solid-state light emitting element 11_1 in the vertical direction.

$$A<B \quad (2)$$

In the cooling unit 20 configured as described above, air at a predetermined flow rate flows in the chamber 1b forming the ventilation duct by operating the light source cooling fans 26 and 27. The plurality of heat sinks (23a, 23b, 23c, 23d, and 23e) are disposed at predetermined sites in the flow path in the chamber 1b, and the cooling medium (air) flowing through the flow path passes through each heat sink.

The plurality of heat sinks are connected with the plurality of light emitting units (11a, 11b, 11c, 11d, and 11e) of the light source unit 10 through the plurality of heat pipes (24a, 24b, 24c, and 24e) and the plurality of heat receiving parts (22a, 22b, 22c, and 22e) or directly through the heat receiving part 22d. Accordingly, heat generated at the plurality of light emitting units (11a, 11b, 11c, 11d, and 11e) can be discharged through the plurality of heat sinks.

In the light source device 1 of the present embodiment, heights of the plurality of heat sinks from the bottom surface of the housing 1a are set to be lower than a height of the light source unit 10. The height of the light source unit 10 has a constraint due to a height of the connector part 2 connected with the endoscope 100, but the entire device can be downsized in the height direction by reducing the heights of the plurality of heat sinks relative to the light source unit 10.

In the present embodiment, the plurality of heat pipes (24a, 24b, 24c, and 24e) that transfer heat from the heat receiving parts (22a, 22b, 22c, 22d, and 22e) of the light source unit 10 each include at least a set of the two heat pipes of the first heat pipe connected with the heat sink in a substantially horizontal direction, and the second heat pipe which curves downward and is connected with the heat sink below the first heat pipe in the direction of gravity. Accordingly, heat generated at the light source unit 10 can be effectively transferred to a heat sink disposed at a position lower than the light source unit 10 and can be discharged, which can prevent increase in the size of the device and contribute to higher improvement of cooling performance.

Moreover, since the first heat pipe connected at a position closer to the solid-state light emitting element is configured as a heat pipe having heat transfer performance higher than the heat transfer performance of the second heat pipe connected at a position relatively separated from the solid-state light emitting element, heat can be efficiently transferred to a heat sink disposed at a position lower than the light source unit 10.

In the light source device 1 of the present embodiment, since the control unit 4 is disposed above the plurality of heat sinks and the power source unit 3 is disposed below the light source unit 10, a limited internal space of the housing 1a can be effectively used to prevent increase in the size of the device and contribute higher improvement of cooling performance

What is claimed is:

1. A light source device comprising:
a housing;
a light source unit disposed at a predetermined height from a bottom surface of the housing;
a heat generation body disposed in the light source unit;
a heat sink disposed at a predetermined height from the bottom surface of the housing; and
a heat pipe connected with the heat generation body and the heat sink, wherein
a height of the heat sink from a reference surface when the reference surface is the bottom surface of the housing is set to be lower than a height of the light source unit from the reference surface, and
the heat pipe includes
a first heat pipe, a first end part of which is connected with the heat generation body and a second end part of which is connected with the heat sink, and
a second heat pipe, a third end part of which is connected with the heat generation body and a fourth end part of which is connected with the heat sink so that a distance to the second end part is longer than a distance between the first end part and the third end part.

2. The light source device according to claim 1, wherein
the first heat pipe is connected by a first fixation member of the heat sink,
the second heat pipe is curved downward in a direction of gravity and is connected by a second fixation member of the heat sink,
the first fixation member is disposed on a first surface parallel to the bottom surface of the housing,
the second fixation member is disposed on a second surface parallel to the bottom surface of the housing, and
a height of the second surface from the reference surface is set to be lower than a height of the first surface from the reference surface.

3. The light source device according to claim 2, wherein the first heat pipe is included in plurality, and at least one of the plurality of first heat pipes is disposed on the first surface.

4. The light source device according to claim 3, wherein
a chamber in which the heat sink is housed is disposed in the housing, and
a height of the chamber from the reference surface is set to be equal to or lower than the height of the light source unit from the reference surface.

5. The light source device according to claim 4, wherein
a light emitting element is included as the heat generation body,
a heat receiving part that transfers heat from the light emitting element includes a first connection part connected with the first heat pipe, and a second connection part connected with the second heat pipe, and
the first connection part is disposed at a distance closer to the light emitting element than the second connection part.

* * * * *